United States Patent [19]

Tecott et al.

[11] Patent Number: 5,021,335

[45] Date of Patent: Jun. 4, 1991

[54] IN SITU TRANSCRIPTION IN CELLS AND TISSUES

[75] Inventors: Laurence Tecott, Norwalk, Conn.; Jack D. Barchas, Stanford; James Eberwine, Menlo Park, both of Calif.

[73] Assignee: The Board of Trustees of the Leland Stanford Junior University, Stanford, Calif.

[21] Appl. No.: 208,267

[22] Filed: Jun. 17, 1988

[51] Int. Cl.[5] ............................................. C12Q 1/68
[52] U.S. Cl. .......................................... 435/6; 435/4; 435/172.2; 435/172.3; 435/91; 436/27; 935/16; 935/18; 935/19; 935/93
[58] Field of Search ................ 435/4, 6, 172.2, 172.3, 435/91; 436/27; 935/16, 18, 19, 39, 320, 93

[56] References Cited

U.S. PATENT DOCUMENTS 4,886,741 12/1989 Schwartz ................................ 435/5

OTHER PUBLICATIONS

Maniatis T., Fritch E., and Sambrook (1982), Molecular Cloning: A Laboratory Manual, pp. 213-216 and pp. 224-235.
Pardue M. L. (1987) in: Hames B & Higgins S., "Nucleic Acid Hybridisation: A Practical Approach", Chap. 8, pp. 179-202.
Eberwine, et al., "Isolation of Enzyme cDNA Clones by Enzyme Immunodetection Assay: Isolation of a Peptide Acetyltransferase", in PNAS, 84:1449-1453 (1987).
Saiki et al., "Primer-Directed Enzymatic Amplification of DNA with a Thermostable DNA Polymerase", in Science, 239:487 (1988).
Baltimore, "Viral RNA-dependent DNA Polymerase", in Nature, 226:1209 (1970).
Tecott, L. (1988) In Situ Transcription: Specific Synthesis of Complementary DNA in Fixed Tissue Sec., Science 240:1661-64.

Primary Examiner—Robert A. Wax
Assistant Examiner—Miguel H. Escallon
Attorney, Agent, or Firm—Bertram I. Rowland

[57] ABSTRACT

In situ transcription is provided by hybridizing cells or tissue with a primer, and extending the primer bound to any template mRNA or DNA with reverse transcriptase or DNA polymerase in the presence of labeled nucleotides, which allows for detection of cells containing the template. The resulting cDNA may be eluted and used in a polymerase chain reaction for isolation of the DNA, and/or the cDNA electrophoresed, which may provide for information concerning the sequence, or the like. This invention was supported by the NIMH, NIDA and ONR grants, and the government may have rights in this invention.

2 Claims, No Drawings

IN SITU TRANSCRIPTION IN CELLS AND TISSUES

INTRODUCTION

1. Technical Field

The subject invention concerns in situ transcription for cDNA synthesis in fixed cells.

2. Background of the Invention

The rapid advances in molecular biology have opened up many avenues for investigation of a wide variety of physiological processes. In order to understand how various cells fulfill their functions, methods are being devised which allow for the detection of genes. One method has been the isolation of tissue, extraction of messenger RNA and the reverse transcription of the messenger RNA to produce cDNA. The cDNA may then be copied to provide double stranded(ds) cDNA which may be cloned. By traditional techniques, one often cannot identify the expression of a particular nucleic acid gene product in a subset of cells without a dilution effect resulting from tissue homogenization. Nor can they be used to identify individual cells containing a particular nucleic acid sequence. There is, therefore, substantial interest in being able to detect in tissue the distribution of expression of one or more products, as well as the ability to identify these products and obtain genes which may be used to express the products for further analysis and characterization.

RELEVANT LITERATURE

Reverse transcriptase can be used to produce a DNA sequence from RNA. Baltimore, *Nature* (1970) 26:1209. The polymerase chain reaction is described by Saiki et al., *Science* (1988) 239:487. See also, Eberwine, et al., *Proc. Natl. Acad. Sci. USA* (1987) 84:1449–1453.

SUMMARY OF THE INVENTION

In situ transcription is provided in which reverse transcription of mRNA is achieved in tissue sections or cells. Tissue sections or cells are obtained, the mRNA in the cells hybridized with an appropriate primer, and then contacted with reverse transcriptase, employing labeled nucleotides, particularly radioactive labels. The resultant signal intensities may be related to the level of mRNA in specific portions and/or cells of the section, while the transcripts may be eluted from tissue sections for a variety of uses.

DESCRIPTION OF THE SPECIFIC EMBODIMENTS

In accordance with the subject invention, in situ transcription is performed with tissue sections. The tissue sections are contacted with a nucleotide primer under hybridizing conditions, followed by contacting with reverse transcriptase under primer-extension conditions. By employing a label, particularly radioactive nucleotides, the primer extension can be followed in the tissue section, demonstrating those cells and sections in the tissue in which the mRNA's are present and providing a qualitative estimation of the mRNA present. If desired, the transcripts may be isolated by elution and used in cloning, for expression, or the like.

The tissue sections may be obtained by any convenient manner: cryostat sections, microtome slices or the like may be prepared. The source of tissue may be any solid organ, such as brain, spleen, bone, heart, vascular, lung, kidney, liver, pituitary, endocrine glands, lymph node, dispersed primary cells, tumor cells, or the like. The tissue may be pretreated in conventional ways prior to sectioning to provide the tissue section sample. Usually a tissue section will be at least about 1 $\mu$m thick, and not more than about 50 $\mu$m usually not more than about 25 $\mu$m, and preferably from about 5 to 15 $\mu$m thick. The section may then be fixed by convenient techniques which do not interfere with the subsequent processing. Conveniently, aldehyde (e.g. dilute aqueous formaldehyde or acetaldehyde) fixing or other conventional technique may be employed. The particular manner in which the tissue is fixed is not critical to this invention, so long as the procedure does not destroy the mRNA, nor interfere with the subsequent steps of the process.

After the tissue is fixed, it may then be hybridized with the appropriate primer. Where it is desired to obtain polyadenylated mRNA, a poly-T primer may be employed. For the most part one will be interested in one or a few mRNA's and in this situation a specific oligonucleotide or a mixture of oligonucleotides coding for a single oligopeptide may be employed. Depending upon the specificity desired, various levels of stringency may be employed in the hybridization. The stringency may be as a result of elevated temperatures, salt concentrations, organic solvents, or the like. Conveniently, the hybridization medium may have from about 10 to 75% of a polar organic solvent, e.g., formamide. Salt concentrations will generally vary from about 0.4M to 1M. The time for the reaction will generally vary from about 1 to 48 hours, more usually from about 6 to 24 hours. The temperature will generally vary from about 20° to 60°, more usually from about 20° to 40° C. The amount of primer will vary widely, generally from about 0.1 ng, more usually from about 0.1 to 25 ng per tissue section of 30 $\mu$L volume of tissue of the hybridizing medium. The volume employed will vary depending on the size of the tissue section, usually within the range of about 5 to 200 $\mu$l, and more usually from about 5 to about 100 $\mu$l.

The primer will generally be at least about 12 nucleotides (nt), and usually not more than about 200 nt, more usually not more than about 100 nt and preferably not more than about 50 nt. The primer may be labeled or unlabeled, conveniently unlabeled or are radioactive, or the like. If labeled, various labels may be employed which have a specific receptor which may be detected or are radioactive or the like. For example, the probe may be labeled with biotin, which may subsequently be bound with avidin which may be labeled with fluorescers, enzymes, or the like. Fluorescers of interest may include phycobiliproteins, fluorescein, or the like. Enzymes may include horseradish peroxidase, phosphatase, or the like. Where the enzyme is likely to be encountered in the tissue cells, prior to hybridization, the protein of the tissue may be denatured. Denaturation can be achieved with heat, specific denaturants, or the like. In some instances the manner in which the tissue was fixed will suffice for denaturation.

Once the hybridization has been carried out, the sections may be washed one or more times, where the washes may provide for the desired stringency. Generally, the washes will have a salt concentration which may be the same as or less than the salt concentration employed during the hybridization and may have a temperature in the range employed for the hybridization, preferably from about 25° to 45° C. Desirably, the washes may be monitored to detect the continued presence of the primer in the wash.

Reverse transcription may then be carried out under conventional conditions for reverse transcriptase. Reverse transcriptase is commercially available and the supplier provides the preferred conditions. Conveniently, the reverse transcription may be carried out at an elevated temperature, in the range of about 25° to 40° C. for a time in the range from 0.1 to 6 h, more usually from about 0.5 to 3 h.

Instead of reverse transcriptase, a DNA polymerase may be used which is functional in the cell. Either an intact DNA polymerase or a functional fragment thereof, e.g. the Klenow fragment, may be employed. Various DNA polymerases are commercially available and may be used in accordance with conventional conditions. While throughout this specification, cDNA will be referred to as copied from mRNA, it is to be understood that DNA may also be copied to provide dsDNA, with the complementary strand being the equivalent of the cDNA reverse transcribed strand.

Included in the reaction mixture will be the necessary deoxynucleotide triphosphates where one or more of the nucleotides may be labeled, particularly with a radioactive label, such as $^{35}S$, $^{32}P$, $^{3}H$, or the like. Alternatively, nucleotides may be obtained which are labeled with biotin, where these nucleotides will become incorporated in the extended chain. The biotin may then be used for binding to avidin, which is labeled with an appropriate, label capable of providing for detection, as described previously. After completion of the reverse transcription, the sections are thoroughly washed to remove any of the labeled nucleotide monomer. Washes will generally be dilute salt solutions less than about 0.25M, at ambient or elevated temperatures, usually not exceeding about 60° C.

Depending upon the nature of the label, the sections may be treated differently. Where a radioactive label is employed, the section may be dehydrated and apposed to appropriate x-ray film. With other labels, the tissue section may be soaked with the appropriately labeled receptor for a sufficient time for specific binding to occur, followed by thorough washing, so as to ensure the complete removal of any non-specifically bound labeled receptor. The washes may be selected so as to selectively remove the labeled receptor without removing the receptor bound to the nucleic acid.

To characterize the transcripts, various procedures may be employed. The transcripts may be eluted from the sections and separated on a denaturing gel. The cDNA transcripts are found to form a complex banding pattern in at least some instances. Desirably, the cDNA may be modified to provide a template which may then be used in a polymerase chain reaction to greatly expand the amount of cDNA produced. The resulting cDNA may be used for further cloning, expression, or the like. The subject methodology can obviate the need to make cDNA libraries of high complexity for specific cDNA isolation. The subject method provides for the direct transcription of messenger RNA in tissue in accordance with the selection of the primer. Thus, only one or a few different sequences will be obtained, which may vary as to the degree of their extension.

The banding pattern in the electrophoresis may also afford an opportunity for differentiation of various messenger RNA's. Patterns may be associated with unique structural aspects of the template, being, for example, related to viral subtypes, alternately spliced products, secondary structure, association of binding proteins, such as ribosomes with the mRNA, or the like. Thus, the subject method may be used in a variety of ways to evaluate a physiological status of cells in tissue sections to identify the pattern of expression of one or more proteins in the cells and tissue sections, to provide for the isolation of genes encoding for a protein encompassing a particular oligopeptide, or the like.

The following examples are all by way of illustration, not by way of imitation.

EXPERIMENTAL

Cryostat sections (11 μm thick) were prepared from fresh frozen rat pituitaries. Sections were fixed for 5 min in 3 percent neutral buffered paraformaldehyde. In situ hybridization was performed for 12 to 16 hours at room temperature in a mix consisting of 4×SSC/50% formamide, to which was added one ng unlabeled oligonucleotide in 25 μl. Sections were washed with two changes in 2×SSC for 30 min at room temperature, followed by washes in 0.5×SSC at 40° C. for two hours with one change. Reverse transcription was performed at 30° C. for one hour in a reaction mix consisting of 15 mM tris-HCl, pH 8.3, 6 mM $MgCl_2$, 40 mM KCl, 7.5 mM dithiothreitol, 250 mM dATP, dTTP and dGTP, 300 μCi/ml α—[$^{35}$S]dCTP (1,000 Ci/mmol, Amersham), 0.12 units ribonuclease inhibitor (RNasin)/μl (BRL, Bethesda, Md.), and 600 units/ml avian myoblastosis virus reverse transcriptase (Seikagaku, St. Petersburg, Fla.). Sections were then washed, with two changes of 2×SSC for 30 min each at room temperature followed by washes in 0.5×SSC at 40° C. for 6 hours with two changes. Sections were then dehydrated and apposed to Kodak XAR x-ray film for 10 min prior to development.

Drug treatments: Rats received daily intraperitoneal injections of bromocriptine (Sandoz) (3 mg/kg body weight), haloperidol (McNeil) or vehicle for four days and were sacrificed 24 hours after the last injection.

For localization by emulsion autoradiography, the above procedure was followed, except that 60 μCi/ml α—[$^{3}$H]dCTP (50 Ci/mmol, Amersham) replaced the $^{35}$S-labeled nucleotide in the reverse transcriptase reaction. The section was dipped in Kodak NTB2 nuclear track emulsion diluted 1:1 with water. Following a 15-hour exposure, the autoradiogram was developed in Kodak D19 for 2 min at 17° C. and fixed in Kodak fixer for 5 min at 17° C. Counterstaining was performed with hematoxylin and eosin.

For electrophoresis of the transcripts, the following procedure was employed: The procedure was performed as described above, except that 300 μCi/ml α—[$^{32}$P]dCTP (410 Ci/mmol, Amersham) replaced α—[$^{35}$S]dCTP in the reverse transcriptase reaction. For gel electrophoresis, transcripts were denatured by incubating sections in (50 μl per section) 4M guanidine-HCl/1M β-mercaptoethanol for 1 hour at 23°. This was followed by protein extraction with 0.5 vol phenol/0.5 vol chloroform, with subsequent ethanol precipitation (10 mg/ml glycogen, 2 vol ethanol, 30 min in dry ice) prior to electrophoresis.

The proopiomelanocortin (POMC) mRNA was used to evaluate the subject method. The POMC gene gives rise to a family of biologically active peptides including adrenocorticotropin, β-endorphin and α-melanocyte-stimulating hormone. An oligonucleotide 36-nt in length, complementary to the sequence encoding amino acids 100 to 111 of rat POMC was used as the primer.

After in situ hybridization to rat pituitary tissue as described above, a strong signal was observed in the intermediate lobe consistent with the known localization of POMC mRNA. When the primer was omitted from the hybridization mix, the signal was not observed. Omission or heat-inactivation of the reverse transcriptase also eliminated the signal. As a negative control, reverse transcription was performed after a hybridization step with a 36 nt probe complementary to tyrosine hydroxylase mRNA, which has not been detected in the rat pituitary. No signal above background was produced. As a positive control, hybridization was performed with a polythymidine (poly-T oligomer) 36 nt in length. Intense signals in both the anterior and intermediate lobes were observed, consistent with the abundance and expected distribution of poly(A+) mRNA.

To further confirm the specificity of the POMC signal, in situ transcription was performed in pituitary sections from animals that had been treated with the dopamine antagonist haloperidol and the dopamine agonist bromocryptine. Various samples were employed and electrophoresed:

(A) 5% polyacrylamide/7M urea gel, 3000 cpm loaded per lane: transcripts resulting from priming with
  (a) no oligonucleotide;
  (b) heterologous 36 nt oligonucleotide;
  (c) POMC oligonucleotide.
(B) 5% polyacrylamide/7M urea gel: comparison of
  (d) POMC-primed cDNA transcribed in the presence of $\alpha$-[$^{32}$P]dCTP (3000 cpm loaded); and
  (e) transcripts primed by a 5'-end, $^{32}$P-labeled POMC oligonucleotide (specific activity, $2 \times 10^8$ cpm/$\mu$g), followed by reverse transcription in the presence of 250 $\mu$M unlabeled deoxynucleotides (900 cpm loaded).
(C) 6% polyacrylamide/7M urea gel: comparison of
  (f) POMC-primed transcripts after elution from tissue; and
  (g) POMC-primed transcripts after elution from tissue and hybridization to POMC cDNA that had been immobilized on nitrocellulose filters; after hybridization in 30% formamide, 5×SSC, 100 $\mu$g/ml salmon sperm DNA and 5×Denhardts, the filters were washed in 2×SSC, 0.1% SDS for 30 min at 37° C. followed by 2 washes in 0.2×SSC, 0.1 SDS for 30 min at 42° C., and the bound transcripts were eluted by incubating the filter in a solution containing 0.1% SDS, 0.5 mM EDTA at 65° C. for 30 min, followed by ethanol precipitation; and
  (h) transcripts that did not hybridize to the POMC-cDNA-bound filter.

The intensities of the intermediate-lobe signals varied in a manner consistent with the known dopaminergic regulation of POMC mRNA. The neuroleptic haloperidol, which elevates POMC mRNA levels, increased the intermediate lobe signal relative to control. Conversely, the dopamine agonist bromocryptine greatly reduced the signal, consistent with the effect of this drug on intermediate lobe POMC mRNA levels.

High intensities of the intermediate-lobe POMC signal were observed. Exposure times of 10 min were required for film autoradiograph with $^{35}$S-labeled transcripts, in contrast with the 3-hour exposures required for in situ hybridization with 3'-end, $^{35}$S-labeled oligonucleotide probes. When the subject reaction was performed in the presence of tritiated deoxycytidine, an emulsion autoradiographic exposure of only 15 hours was sufficient for the cellular localization of silver grains in the intermediate lobe. The increase in signal intensity relative to standard protocols likely resulted from the incorporation into the transcripts of many radio-labeled deoxynucleotides (approximately 25% of incorporated deoxynucleotides) per mRNA molecule.

A primer-independent background signal was observed, which did not require a hybridization step prior to the enzyme reaction, but did require reverse transcriptase. This suggests that endogenous sites occurred in the tissue section, serving as primer-template complexes for the initiation of reverse-transcriptase activity.

To further characterize the transcripts produced in the POMC reaction, radiolabeled POMC oligonucleotide-primed transcripts were eluted from pituitary sections and separated on a denaturing gel. The cDNA transcripts from POMC primer formed a complex banding pattern, while transcripts produced after hybridization with the heterologous tyrosine hydroxylase oligonucleotide produced a smear of radioactivity, similar to that of the unprimed sample.

To determine whether the bands represented extensions of the oligonucleotide primer, hybridization with a 5'-end $^{32}$P-labeled POMC oligonucleotide was performed, followed by reverse transcription in the presence of high concentrations of unlabeled deoxynucleotides. The resulting transcripts produced a similar autoradiographic pattern of bands, thus demonstrating that they resulted from extension of the oligonucleotide primer.

To determine whether the POMC oligonucleotide-primed transcripts were cDNA copies of POMC mRNA, the denatured transcripts were hybridized to single-stranded POMC cDNA that had been immobilized on nitrocellulose filters. After high-stringency washes, the hybridized transcripts were eluted from the filter and electrophoresed on a polyacrylamide-urea gel. The banding pattern prior to hybridization was similar to that observed for transcripts that had hybridized to POMC cDNA, whereas the non-hybridizing transcripts did not produce bands on electrophoresis. This identified the bands as sequences complementary to POMC cDNA.

It was further shown that the specific cDNA's produced by the in situ transcription reaction may be denatured and eluted from tissue sections for cloning. It was possible to clone POMC cDNA from 3 11 $\mu$-thick pituitary sections using the following method: After eluting from the 3 pituitary sections, the second-strand cDNA was synthesized by self-priming (Efstratiatis et al., *Cell* (1976) 7:279). This was followed by blunt-ending of the double-stranded cDNA with T$_4$ DNA polymerase and subsequent restriction of the cDNA with HaeIII. (Seeburg et al., *Nature*, 220:486). These fragments were then cloned into SmaI-linearized pSP64, whereupon transformation into DH5a cells, followed by colony lifts and hybridization with a POMC gene-fragment probe (Roberts et al. in *Recent Progress in Hormone Research* (Academic Press, NY, 1982), p. 227) revealed that 40% of the insert-containing transformants contained POMC cDNA. The cDNA was approximately 70 nt in length and resulted from cloning of the HaeIII fragment closest to the primer site. (Drouin and Goodman, *Nature* (1980) 288:610).

Since these sections contained roughly 4.5 ng of poly-(A+)RNA, cloning of specific cDNA's by in situ transcription may be achieved with a smaller amount of tissue than is required by other methods, which usually require greater than about 1 µg of poly(A+) mRNA.

The subject technique may be used for cloning human cDNA's from limited quantities of tissues obtained pre- or post-mortem to determine the precise anatomical localization of mRNA's and to demonstrate the specificity of transcription in tissues having a complex population of mRNA's, such as the brain. In addition, the subject technique may be combined with the polymerase chain reaction to avoid making highly complex cDNA libraries, to provide for convenient amounts of copies of rare mRNA, or the like.

It is evident from the above results that the subject invention provides for a highly efficient manner for obtaining a large amount of information about transcription products from cells in tissue. The method provides for anatomical localization of the cells involved in transcription. In addition, the cDNA's produced may be eluted and used in a variety of ways. The eluted cDNA's may be electrophoresed, whereby a unique pattern of bands may be obtained. The band pattern may provide for differentiation of viral subtypes or alternate splice-products of a single gene, information concerning the secondary structure of the template or association of ribosomes or other proteins with the mRNA, or the like.

Although the foregoing invention has been described in some detail by way of illustration and example for purposes of clarity of understanding, it will be obvious that certain changes and modifications may be practiced within the scope of the appended claims.

What is claimed is:

1. A method for determining the occurrence of transcription of a target DNA sequence in cells in a fixed tissue section, said method comprising:

contacting said tissue section with a primer complementary to a sequence in the 3' proximal region MRNA of said DNA sequence;

contacting said tissue section containing said primer with reverse transcriptase and deoxynucleotide triphosphates, wherein at least one of the triphosphates is labeled with a label to provide a detectable signal, whereby cDNA is produced by extension of said primer;

washing said tissue to remove substantially all of said triphosphates present in said tissue; and detecting the presence of said cDNA in cells in said tissue by means of said label.

2. A method according to claim 1, wherein said label is a radioactive label.

* * * * *